United States Patent [19]
Froehler

[11] Patent Number: 5,256,775
[45] Date of Patent: Oct. 26, 1993

[54] EXONUCLEASE-RESISTANT OLIGONUCLEOTIDES

[75] Inventor: Brian C. Froehler, Belmont, Calif.

[73] Assignee: Gilead Sciences, Inc., Foster City, Calif.

[21] Appl. No.: 555,522

[22] Filed: Jun. 5, 1990

Related U.S. Application Data

[63] Continuation-in-part of Ser. No. 361,045, Jun. 5, 1989, abandoned.

[51] Int. Cl.$^5$ ............................................. C07H 21/02
[52] U.S. Cl. .................... 536/25.6; 536/23.1; 536/25.33
[58] Field of Search ........................... 536/27-29

[56] References Cited

FOREIGN PATENT DOCUMENTS

| | | |
|---|---|---|
| 0061746 | 6/1982 | European Pat. Off. . |
| 219342A2 | 4/1987 | European Pat. Off. . |
| WO86/07362 | 12/1986 | PCT Int'l Appl. . |
| WO88/00201 | 1/1988 | PCT Int'l Appl. . |
| WO89/05358 | 6/1989 | PCT Int'l Appl. . |

OTHER PUBLICATIONS

P. Verspieren et al., *Gene* 61:307-315 (1987).
Agrawal, *Tet. Lett.* 28(31):3539-3542 (1987).
Brill et al., *Tet. Lett.* 29(43):5517-5520 (1988).
Froehler, *Tet. Lett.* 27(46):5575-5578 (1986).
Froehler et al., *Nuc. Acids Res.* 14(13):5399-5407 (1986).
Froehler et al., *Nuc. Acids Res.* 16(11):4831-4839 (1988).
Letsinger et al., *Nuc. Acids. Res.* 14(8):3487-3499 (1986).

*Primary Examiner*—Johnnie R. Brown
*Assistant Examiner*—L. Eric Crane
*Attorney, Agent, or Firm*—Morrison & Foerster

[57] ABSTRACT

A method is provided for making 3' and/or 5' end-capped oligonucleotides so as to render the oligonucleotide resistant to degradation by exonucleases. The exonuclease degradation resistance is provided by incorporating two or more phosphoramidate and phosphorocmonothioate and/or phosphorodithioate linkages at the 5' and/or 3' ends of the oligonucleotide, wherein the number of phosphoramidate linkages is less than a number which would interfere with hybridization to a complementary oligonucleotide strand and/or which would interfere with RNAseH activity when the oligonucleotide is hybridized to RNA.

20 Claims, No Drawings

EXONUCLEASE-RESISTANT OLIGONUCLEOTIDES

CROSS-REFERENCE TO RELATED APPLICATIONS

This application is a continuation-in-part of U.S. patent application Ser. No. 07/361,045, filed 5 Jun. 1989, now abandoned, the disclosures of which are incorporated by reference herein. This application also claims priority to international application PCT/US90/03138, filed 5 Jun. 1990.

TECHNICAL FIELD

The present invention is directed to oligonucleotides containing a 3'- and/or 5'-capped terminal and which are thereby rendered resistant to degradation by exonucleases. The exonuclease-resistant oligonucleotides have two or more phosphoramidate internucleotide linkages at one or both termini which render the oligonucleotides resistant to degradation.

BACKGROUND

DNA molecules contain internucleotide phosphodiester linkages which are degraded by exonucleases present in cells, culture media and human serum. For example, degradation by exonucleases in tissue culture media of DNA may be observed within about 30 minutes to about six hours. Synthetic oligodeoxynucleotides with phosphodiester linkages are routinely used in genetic engineering, for example, to locate specific RNA or DNA fragments from a library. The long-term stability of an oligonucleotide for this utility is not a major concern, since the oligonucleotide is usually not exposed to the relatively stringent environment of the culture medium, therefore exonuclease degradation is not a substantial problem.

However, it is in fact frequently desirable to produce oligodeoxynucleotides which are stable (i.e., for more than several hours or days) for long-term uses. For example, a oligodeoxynucleotide with phosphodiester linkages can be used to block protein synthesis by hydrogen bonding to complementary messenger RNA thereby providing a tool for use in an antisense fashion. Exonuclease-stable oligodeoxynucleotides could also be utilized to form triple-helix DNA which would interfere with the transcription process or with DNA replication, by competing with naturally occurring binding factors or by gene destruction. However, in order to utilize synthetic oligonucleotides in this manner, they must be stable to exonucleases, the major activity of which in cells and serum appears to be 3' to 5', i.e., digestion of oligonucleotides begins starting at the 3' end.

The present invention is accordingly directed to such exonuclease-stable oligonucleotides.

RELATED ART

The following references relate to one or more aspects of the presently claimed invention:

Froehler, *Tet. Lett.* 27(46):5575–5578 (1986), describes polymer-bound deoxynucleoside H-phosphonate diesters as precursors to phosphoramidate, thiophosphate and phosphate triester analogs of DNA.

Froehler et al., *Nuc. Acids Res.* 16(11):4831–4839 (1988), describe the synthesis of a 15-mer containing 12 phosphoroamidate linkages derived from primary and secondary amines. The chemistry of the process is summarized in the figure shown on page 4833 of the reference.

Froehler et al., *Nuc. Acids Res.* 14(13):5399–5407 (1986), describe the synthesis of deoxyoligonucleotides via deoxynucleoside H-phosphonate intermediates. The chemistry of this process is essentially shown in scheme 2 on page 5401 of the reference.

Froehler, European Patent Publication No. 219342-A2, published 2 Apr. 1987, is similar to the teachings of the latter two references in that the synthesis of DNA Via deoxynucleoside H-phosphonate intermediates is shown.

Letsinger et al., *Nuc. Acids Res.* 14(8):3487–3499 (1986), describe complexes of polyuridylic acid (poly U) and polythymidylic acid (poly dT) with oligonucleotides possessing different pendant groups that are linked to the oligonucleotide chain at the internucleotide phosphodiester linkages.

Stein et al., *Nuc. Acids Res.* 16(8):3209–3221, (1988) present a study of oligodeoxynucleotides modified so as to contain phosphorothioate linkages. The authors, in addition to evaluating a number of other physicochemical properties of such oligonucleotides, study the susceptibilities of the compounds to a number of endonucleases and exonucleases. The authors found a significant decrease in the $T_m$ of fully substituted phosphorothioate oligodeoxynucleotides compared to diester controls (FIG. 3), i.e., a 15°–20° C. decrease in $T_m$ and a 30–40 Kcal/mole decrease in $\Delta H$ for fully substituted molecules (p. 3215).

Brill et al., *Tet. Lett.* 29(43):5517–5520 (1988) describe the preparation of dinucleoside phosphorodithioates by sulfur oxidation of thiophosphate triesters.

Agrawal, *Tet. Lett.* 28(31):3539–3542 (1987) describe the automated synthesis of oligodeoxynucleosides containing methylphosphonate linkages, using nucleoside methylphosphonamidites as starting materials. The authors conclude that two adjacent methylphosphonate linkages at the 3' end provides protection against degradation by snake venom phosphodiesterase and spleen phosphodiesterase (and, like Stein et al., the authors do not evaluate nuclease stability of the oligonucleotides in serum, tissue culture medium or cells).

PCT publication WO89/05358, inventors Walder et al., describe oligodeoxynucleotides modified at the 3' terminus so as to render the oligonucleotide chain resistant to degradation within cells and body fluids. Disclosed modifications at the 3'-terminal phosphodiester linkage include replacement of that linkage with an alkyl or aryl phosphotriester, hydrogen phosphonate, an alkyl or aryl phosphonate, an alkyl or aryl phosphoramidate, a phosphorothioate, or a phosphoroselenate, although the preferred modification is stated to be the incorporation of a 3'-terminal phosphotriester linkage.

DISCLOSURE OF THE INVENTION

Accordingly, it is a primary object of the invention to address the above-mentioned need in the art and to provide exonuclease-resistant oligonucleotides.

It is another object of the invention to provide exonuclease-resistant oligonucleotides modified at the 3'-terminus so that the initially present phosphodiester linkages are replaced with a specified number of phosphoramidate linkages.

It is still another object of the invention to provide such exonuclease-resistant oligonucleotides which additionally contain phosphoromonothioate and/or phosphorodithioate linkages.

It is yet another object of the invention to provide exonuclease-resistant oligonucleotides which are capable of hybridizing to a complementary oligonucleotide strand.

It a further object of the invention to provide methods of making such exonuclease-resistant oligonucleotides.

It is still a further object of the invention to provide a method for end-capping oligonucleotides with moieties which can perform multiple functions, such as aiding in transport, serving as chromophoric tags, or enabling cross-linking.

Additional objects, advantages and novel features of the invention will be set forth in part in the description which follows, and in part will become apparent to those skilled in the art upon examination of the following, or may be learned by practice of the invention.

In a first aspect, the present invention provides oligonucleotides having two or more phosphoramidate linkages at the 3' terminus and/or 5' terminus, which oligonucleotides are resistant to exonuclease degradation. The number of phosphoramidate linkages is at least 1 and less than a number which would interfere with hybridization to a complementary oligonucleotide strand, and/or less than a number which would interfere with RNAse activity when said oligonucleotide is hybridized to RNA. Preferably, at least 2, and more preferably on the order of about 2 to 10, phosphoramidate linkages are incorporated at either or both the 3' terminus and the 5' terminus. The phosphoramidate linkages may be substituted with any one of a number of different types of moieties as will be described in detail hereinbelow.

In another aspect, exonuclease-resistant aligonucleotide are provided which have the following formulas I, II or III, i.e., containing phosphoramidate linkages as just described as well as phosphoromonothioate and/or phosphorodithioate linkages:

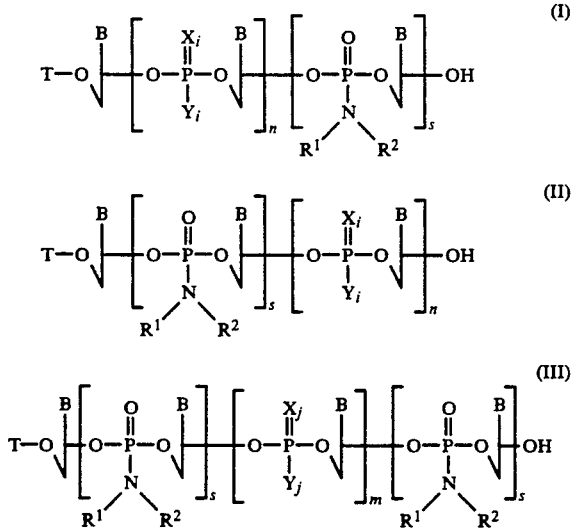

wherein each n, m, i, j and s is independently an integer and each s is in the range of about 2 to 10; each n and m is independently from 1 to about 50; s+n in formulas I and II is less than 100; and s+s+m in formula III is less than about 100; each i varies from 1 to n; each j varies from 1 to m; T is hydrogen or a hydroxyl-protecting group; $R^1$ and $R^2$ are moities independently selected from the group consisting of hydrogen, hydrocarbyl substituents of 20 carbon atoms or less, and oxyhydrocarbyl of 20 carbon atoms or less and 1-3 oxy groups, wherein said hydrocarbyl and oxyhydrocarbyl substituents are linear or branched alkyl of 1 to 20 carbon atoms, linear or branched alkenyl of 2 to 20 carbon atoms, cycloalkyl or cycloalkenyl of 3 to 20 carbon atoms, linear or branched alkoxy of 1 to 20 carbon atoms, or aryl of 6 to 18 carbon atoms, with the proviso that $R^1$ and $R^2$ are not both hydrogen;

each B is independently a protected or unprotected heterocyclic base;

each $X_i$ and $X_j$ is independently O or S; and each $Y_i$ and $Y_j$ is independently R, —SR or —OR, where R is as defined for $R^1$ and $R^2$.

The present invention also provides methods for preparing such end-capped oligonucleoides.

MODES FOR CARRYING OUT THE INVENTION

As used herein the terms "polynucleotide" and "oligonucleotide" shall be generic to polydeoxyribonucleotides (containing 2'-deoxy-D-ribose or modified forms thereof), to polyribonucleotides (containing D-ribose or modified forms thereof), and to any other type of polynucleotide which is an N-glycoside of a purine or pyrimidine bases, or modified purine or pyrimidine bases. The term "nucleoside" will similarly be generic to ribonucleosides, deoxyribonucleosides, or to any other nucleoside which is an N-glycoside of a purine or pyrimidine base, or modified purine or pyrimidine base. There is no intended distinction in length between the term "polynucleotide" and "oligonucleotide" and these terms will be used interchangeably.

It will be appreciated that as used herein the terms "nucleoside" and "nucleotides" will include those moieties which contain not only the known purine and pyrimidine bases, i.e., adenine, thymine, cytosine, guanine and uracil, but also other heterocyclic bases which contain protecting groups or have been otherwise modified or derivatized.

By "modified nucleosides" or "modified nucleotides" as used herein are intended to include those compounds containing one or more protecting groups such as acyl, isobutyryl, benzoyl, or the like, as well as any of the wide range of modified and derivatized bases as known in the art. Examples of such modified or derivatized bases include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methyladenine, 1-methylpseudouracil, 1-methylguanine, 1-methylinosine, 2,2-dimethylguanine, 2-methyladenine, 2-ethylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 3-(3-amino-3-N-2-carboxypropyl) uracil, and 2,6-diaminopurine.

Modified nucleosides or nucleotides can also include modifications on the sugar moiety, for example, wherein one or more of the hydroxyl groups are replaced with halogen or aliphatic groups, or functionalized as ethers, amines, etc.

The polynucleotides according to the present invention may be of any length, but lengths of about three to about fifty nucleotides are particularly useful for most genetic engineering applications. According to the present invention, the 3' end and/or the 5' end of the polynucleotide will contain at least two phosphoramidate internucleotide linkages. The remaining internucleotide linkages may be phosphodiester linkages, phosphorothioate linkages or phosphorodithioate linkages, or any other internucleotide linkage, other than a phosphoramidate, or combinations of these other linkages. Methods for preparing such non-phosphoramidate linkages are known in the art, e.g., as taught by Froehler et al., Nuc. Acids Res. 14:5399–5467 (1986), and Froehler, B., Tet. Lett. 27:5575–5578 (1986), cited above and incorporated by reference herein.

Internucleotide phosphodiester linkages are prepared from hydrogen phosphonate linkages preferably by oxidation with, e.g., aqueous iodine. A typical procedure involves treatment of the hydrogen phosphonate in 0.1M iodine in Pyr/NMI/H₂O/THF (5:1:5:90) for about 2–3 minutes, followed by treatment with 0.1M iodine in Et₃/H₂O/THF (5:5:90) for another approximately 2–3 minutes.

Phosphoromonothioate linkages are formed from the initially present hydrogen phosphonate linkages by treatment with sulfur. The reaction is carried out at approximately room temperature for on the order of 20 minutes in a solvent system which typically includes a sulfur solvent such as CS₂ along with a basic solvent such as pyridine. Other suitable solvet systems include CS₂/lutidine and CS₂/triethylamine; CS₂ is preferred as the sulfur solvent because it acts to dissolve elemental sulfur. The following scheme illustrates the postulated reaction:

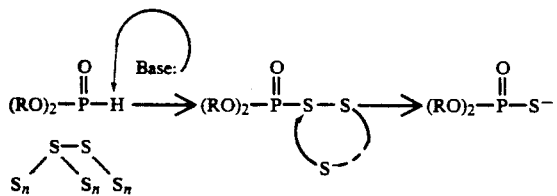

(See, e.g., Stein et al., cited above.)

To form hydrogen phosphorodithioate linkages, sulfurization of the hydrogen phosphoromonothioate linkages is effected using conditions identical to those just described for the preparation of the phosphoromonothioate moiety. (Note: the term "phosphorothioate" as used herein is intended to encompass both "phosphoromonothioate" and "phosphorodithioate" linkages.)

Structure of the End-Capped Oligonucleotides:

The oligonucleotides of the invention, as noted above, are resistant to degradation under both physiological and tissue culture conditions, and in particular are resistant to degradation by exonucleases.

In order that the oligonucleotide be resistant to such enzymatic degradation, it is modified so that phosphodiester linkages initially present at the 3' terminus are replaced with a selected number of phosphoramidate linkages, that number being at least one and less than a number which would cause interference with hybridization to a complementary oligonucleotide strand, and/or less than a number which would interfere with RNAseH activity when said the oligonucleotide is hybridized to RNA. Such a modification may additionally or alternatively be made at the 5' terminus.

It is preferred that the number of phosphoramidate linkages be selected such that the melting temperature of any duplex formed with complement is lowered by less than about 10° C. relative to that obtained with an oligonucleotide containing only the initial phosphodiester linkages. Preferably, the number of phosphoramidate linkages is such that the melting temperature of a duplex formed is lowered by less than about 5° C. The number of phosphoramidate linkages present is typically and preferably between about 2 and 10, more preferably between about 2 and 8, and most preferably between about 2 and 6.

The phosphoramidate linkage has the formula

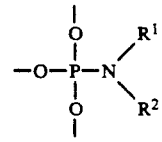

wherein the $R^1$ and $R^2$ moieties are substituents which must be selected so as not to interfere with hybridization with complement. In most cases, the groups $R^1$ and $R^2$ are independently selected from the group consisting of hydrogen, hydrocarbyl substituents of 20 carbon atoms or less, and oxyhydrocarbyl substituents of 20 carbon atoms or less containing 1–3 oxy groups, with the proviso that $R^1$ and $R^2$ are not both hydrogen, i.e., the phosphoramidate linkages herein are always N-substituted. In this case, it is preferred that one of the two substituted. In this case, it is preferred that one of the two substituents by hydrogen. Suitable hydrocarbyl and oxyhydrocarbyl substituents include, for example, linear or branched alkyl of 1–20 carbon atoms, linear or branched alkenyl of 2–20 carbon atoms, cycloalkyl or cycloalkenyl of 3–20 carbon atoms, linear or branched alkoxy of 1–20 carbon atoms, or aryl of 6–18 carbon atoms. The hydrocarbyl substituent may be, for example, an alkoxy substituent having the formula $CH_3O—(CH_2)_x—$ or a straight chain alkyl group having the formula $CH_3(CH_2)_y—$ where x is an integer in the range of 1–20, inclusive, preferably in the range of 1–10, inclusive, and y is an integer in the range of 0–15, inclusive. Examples of preferred oligonucleotide linkages within the aforementioned groups are wherein one of $R^1$ and $R^2$ is H and the other is either 2-methoxyethyl, dodecyl, or n-propyl. (The 2-methoxyethyl and dodecyl linkages are sometimes referred to herein as "MEA" and "C12", respectively.)

The $R^1$ and $R^2$ groups may also be, in addition to the foregoing, macromolecular species such as sugars, polypeptides, chromophoric groups, lipophilic groups, polymers, steroid hormones, or the like.

"Lipophilic" groups refer to moieties which are chemically compatible with the outer cell surface, i.e., so as to enable the oligonucleotide to attach to, merge with and cross the cell membrane. Examples of such lipophilic groups are fatty acids and fatty alcohols (in addition to the long chain hydrocarbyl groups described above).

Examples of preferred polypeptides that can be used for $R^1$ and/or $R^2$ include transferrin and epidermal growth factor (EGF), while suitable non-polypeptide polymers include ionic, nonionic and zwitterionic polymers. Examples of zwitterionic species useful herein include those described in copending, commonly assigned U.S. patent application Ser. No. 07/515/504, filed 27 Apr. 1990 and incorporated herein by reference. Examples of a particularly preferred polymer is polyethylene glycol.

Steroid substituents include any of the general family of lipid compounds which comprise sterols, bioacids, cardiac glycosides, seponans, and sex hormones, which include the following basic structure:

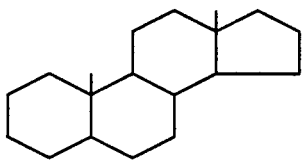

Examples of steroids include natural corticosteroid hormones (produced by the adrenal glands), sex hormones (progesterone, androgens, and estrogens). Other information regarding steroid substituents useful herein may be found in U.S. patent application Ser. No. 07/461,884 entitled "Oligonucleotide-Steroid Hormone Conjugaes," inventors Bird et al., filed 1 Jun. 1990, which is of common assignment herewith and incorporated herein by reference.

These various $R^1$ and $R^2$ groups can confer any of a variety of desired properties to the oligonucleotide. For example, if $R^1$ or $R^2$ is a polymer such as polyethylene glycol, a polypeptide or a lipophilic group such as a long-chain hydrocarbyl moiety, such a group may facilitate transport or permeation of the oligonucleotide through cell membranes, thus increasing the cellular uptake of the oligonucleotide. The $R^1$ or $R^2$ group may also be a group which affects target DNA or RNA to which the oligonucleotide will bind, such as providing covalent linkages to the target strand to facilitate cleavage or intercalation of the oligonucleotide to the target strand. The $R^1$ and $R^2$ groups may additionally serve a cutting function (e.g., a site for cutting the complementary strand), or a receptor function (e.g., a receptor ligand).

It will be appreciated by those skilled in the art that the oligonucleotides of the present invention can include other phosphoramidate N-substituents not explicitly disclosed herein so long as those substituents confer exonuclease resistance and do not interfere with hybridization to a complementary oligonucleotide strand.

The invention also encompasses oligonucleotide compositions containing oligonucleotides of the following formula I, II or III, i.e., wherein phosphoromonothioate and/or phosphorodithioate linkages are incorporated in addition to the phosphoramidate linkages:

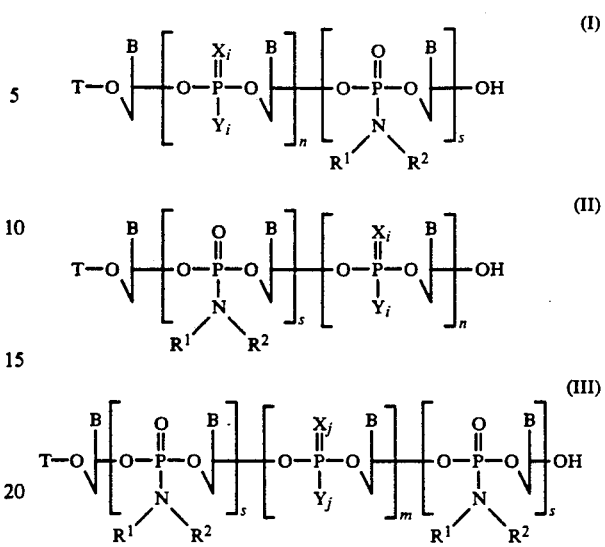

in which B, T, $R^1$, $R^2$, $X_i$, $X_j$, $Y_i$, $Y_j$, n, m, i, j and s are as defined above. In these structures, it is preferred that "s," which defines the number of phosphoramidate linkages, be in the range of 2–8, more preferably in the range of 2–6. It is also preferred that m and n be within the aforementioned ranges.

Synthetic Methods:

According to one embodiment of the present invention, the 3'-capped oligonucleotides may be prepared by first preparing a polymer-bound polynucleoside with the formula IV

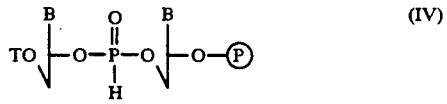

wherein P is a solid state polymeric support, or other type of solid support, and B the base portion of a nucleoside, i.e., a purine or pyrimidine base, or any modified purine or pyrimidine base. As is conventional in oligonucleotide syntheses, the functional groups on the base, i.e., the amine groups, will be appropriately protected during the course of the synthesis and removed after the completed polynucleotide is removed from the polymer support. As is the convention, in the formula shown above in IV, the linkage to the polymer support is through the 3' hydroxy group, the free hydroxy group is the 5' group of the nucleoside. The group T is a conventional hydroxy-protecting group used in oligonucleotide synthesis, preferably the DMT group (dimethoxytrityl) or MMT group (monomethoxytrityl). The polymer-bound polynucleoside hydrogen phosphonate (IV) is preferably prepared by treating the DBU (1,8-diazabicyclo[5.4.0]undec-7-ene ammonium salt) of a 5'-protected (preferably, 5 DMT) nucleoside hydrogen phosphonate with a polymer-bound nucleoside, linked to support through its 3'-hydroxyl group in the presence of an activating agent, as is known in the art. Methods for preparing such polymer-bound polynucleoside hydrogen phosphonates are disclosed, for example, by Froehler, B., et al., *Nuc. Acids Res.* 16:4831–4839 (1988); Froehler, B., et al., *Nuc. Acids Res.* 14:5399–5467 (1986); and Froehler, B., et al., *Nucleosides and Nucleotides* 6:287–291 (1987). Then, one or more nucleoside hydrogen phosphonates may be added (to make the two or more internucleotide linkages at the 3' end of the polynucleotide) by sequentially deprotecting the 5'-hydroxy group of the polymer-bound polynucleotide, and condensing with the next nucleoside hydrogen phosphonate. The oligonucleotide chain elongation will proceed in conformance with a predetermined sequence in a series of condensations, each one of which results in the addition of another nucleoside to the oligomer. The condensation is typically accomplished with dehydrating agents, which are suitably phosphorylating agents or acylating agents such as isobutylchloroformate, diphenylchlorophosphate, organic acid anhydrides (such as acetic anhydride, isobutyric anhydride or trimethyl acetic anhydride) and organic acid halides such as pivaloyl chloride, pivaloyl bromide, 1-adamantylcarboxylic chloride or benzoyl chloride. The preferred condensing agent is pivaloyl chloride in pyridine acetonitrile. Prior to the addition of each successive nucleoside hydrogen phosphonate, the 5'-protecting group or the carrier bound nucleotide is removed. Typically, for removal of the DMT group, this is done by treatment with 2.5% volume/volume dichloroacetic acid/$CH_2Cl_2$, although 1% weight/volume trichloroacetic acid/$CH_2Cl_2$ or $ZnBr_2$-saturated nitromethane are also useful. Other deprotection procedures suitable for other known protecting groups will be apparent to those of ordinary skill in the art.

The carrier is preferably washed with anhydrous pyridine/acetonitrile (1/1,v/v) and the condensation reaction is completed in as many cycles as are required to form the desired number of 3'-end internucleotide bonds which will be converted to phosphoramidates. After the required number of synthetic cycles, the carrier-bound polynucleotide hydrogen phosphonate is oxidized to convert the hydrogen phosphonate internucleotide linkages to phosphoramidate linkages, preferably by treatment with the desired amine $NHR^1R^2$ with $R^1$ and $R^2$ as defined earlier and $CCl_4$ as described in Froehler, et al., *Nucleic Acids Research* 16:4831-4839 (1988). Although carbon tetrachloride is preferred, other mild oxidizing agents may be utilized.

After the oxidation to form the phosphoramidate internucleotide linkages, the oligonucleotide is then completed by methods which form nonphosphoramidate linkages, such as phosphodiester linkages, phosphorothioate linkages or phosphorodithioate linkages, by methods known in the art referenced above and incorporated by reference herein. The preferred method for completing the oligonucleotide is to continue the sequence using 5'-protected nucleoside hydrogen-phosphonates. In the instance where the 5' end will not be capped, after the last 5'-protected nucleoside hydrogen phosphonate has been added, all of the hydrogen phosphonate linkages are oxidized to produce diester linkages, preferably by aqueous iodine oxidation or oxidation using other oxidizing agents, such as N-chlorosuccinimide, N-bromosuccinimide or salts or periodic acid. This will result in all of the internucleotide linkages, except for the 3'-end capped linkages which are phosphoramidate linkages, being phosphodiester linkages. Thereafter, the oligonucleotide may be separated from the carrier, using conventional methods, which in the preferred instance is incubation with concentrated ammonium hydroxide. Any protecting groups may be removed as described above using about 2% dichloroacetic acid/$CH_2Cl_2$, or about 80% acetic acid, or by other conventional methods, depending on the nature of the protecting groups. The desired oligonucleotide is then purified by HPLC, polyacrylamide gel electrophoresis or using other conventional techniques.

The following schemes illustrate various synthetic processes within the scope of the invention:

Scheme 1

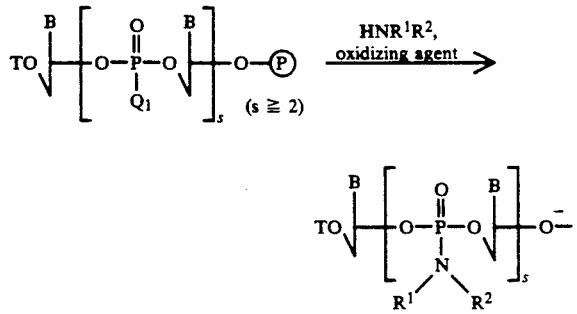

T: protecting group
$\circled{P}$: protecting group or solid state carrier
i: varies from 1 to 5
Q: hydrogen or $-NR^1R^2$ (with the proviso that at least one $Q_i$ is hydrogen)
B: a purine or pyrimidine base
$R^1$, $R^2$: see text Scheme 2a 1) 5' - blocked nucleoside H-phosphate and pivaloyl chloride as activator
2) remove 5' - blocking group
3) $HNR^1R^2$/oxidizing agent
4) optional repetition of steps 1-3

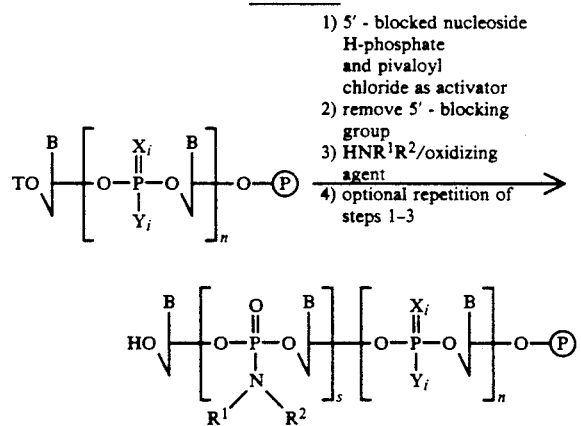

T, $\circled{P}$, $X_i$, $Y_i$, $R^1$, $R^2$ = as defined in text and in Scheme 1

Scheme 2b

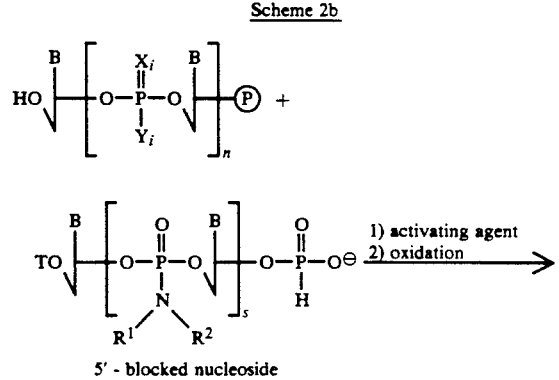

1) activating agent
2) oxidation

5' - blocked nucleoside

-continued
Scheme 2b

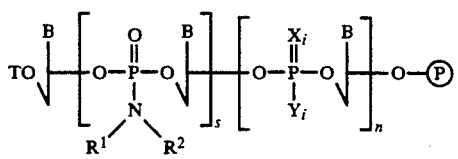

T, $X_i$, $Y_i$, $R^1$, $R^2$, s, n, = as defined in text and in Schemes 1 and 2a

Scheme 3

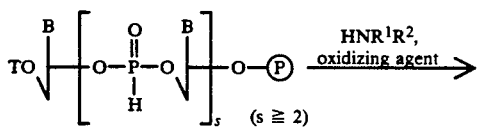

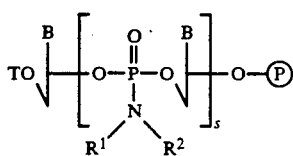

1) remove T
2) condense 5' - blocked nucleoside H-phosphonate, H-phosphorothioate or H-phosphorodithioate with pivaloyl chloride as activator
3) remove 5' - blocking group
4) repeat steps 2) & 3)
5) oxidize to form phosphodiester, phosphorothioate and/or phosphorodithioate linkages
6) condense with additional 5' - blocked nucleoside phosphonates, optionally react with $HNR^1R^2$ in the presence of an oxidizing agent

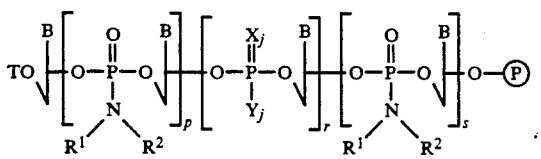

The foregoing discussion has revolved around the consecutive addition of mononucleoside hydrogen phosphonates, but it will be understood that one or more nucleotides can be added in a given cycle by using a polynucleotide, such as a di- or trinucleotide.

It will also be understood that while the above method has been described in connection with use of a solid state carrier if the object oligonucleotide is small, i.e., containing, for example, only five nucleotides (therefore having only four internucleotide linkages, two of which are phosphoramidate linkages) it is feasible to conduct the synthesis without the use of a solid state support. In such an instance a conventional 3'-hydroxy protecting group may be used which is different from the 5'-protecting group used in the synthesis, so that the 5'-protecting group may be selectively removed while the 3'-protecting group remains intact.

It will also be appreciated that the two or more phosphoramidate linkages need not each contain the same $R^1$ and $R^2$ groups. This may be accomplished by generating the first internucleotide hydrogen phosphonate linkage, and then oxidizing it with a first amine, generating the second hydrogen phosphonate internucleotide linkage, and then oxidizing it in the presence of a second (different) amine. This would result in a capped oligonucleotide having mixed phosphoramidate internucleotide linkages.

In another embodiment of the present invention, a 5'-capped oligonucleotide may be made. In such an instance, the above method may be modified by first forming a polymer-bound oligonucleotide having only hydrogen phosphonate internucleotide linkages which may then be oxidized to form phosphodiesters (or phosphorothioate or phosphorodithioate linkages). Then for the last two (or more) cycles, the 5'-end cap is formed when the last two or more nucleosides are added, followed by reaction with the amine $NHR^1R^2$. Alternatively, the 5' end may be added by adding a polynucleotide, such as a tri- or tetranucleotide containing the desired phosphoramidate internucleotide linkages.

In still another embodiment, a combination of both of the above methods for making a 5' and a 3' end-capped oligonucleotide may be utilized. The first two (or more) internucleotide linkages on the 3'-bound oligonucleotide may be oxidized to form the phosphoramidate linkages, then the non-terminal portion of the oligonucleotide may be made (having phosphodiesters, phosphorothioate or phosphorodithioate internucleotide linkages), with the final two (or more) linkages being phosphoramidates, formed as described above.

Methods of Use:

The uses of 5'- or 3'-phosphoramidate-capped oligonucleotides as made in accordance with the present invention may be as therapeutic agents against viral diseases (such as HIV, hepatitis B, cytomegalovirus), cancers (such as leukemias, lung cancer, breast cancer, colon cancer) or metabolic disorders, immune modulation agents, or the like, since the present end-capped oligonucleotides are stable within the environment of a cell as well as in extracellular fluids such as serum, and can be used to selectively block protein synthesis, transcription, replication of RNA and/or DNA which is uniquely associated with the disease or disorder. The end-capped oligonucleotides of the invention may also be used as therapeutics in animal health care, plant gene regulation (such as plant growth promoters) or in human diagnostics, such as to stabilize DNA probes to detect microorganisms, oncogenes, genetic defects, and the like, and as research reagents to study gene functions in animal cells, plant cells, microorganisms, and viruses. There may also be dermatologic applications for treatment of diseases or for cosmetic purposes. There are many other potential uses which derive from the stability of the oligonucleotide to exonuclease degradation, thus prolonging oligonucleotide integrity within the relatively stringent environment of the cells.

It is to be understood that while the invention has been described in conjunction with the preferred specific embodiments thereof, that the foregoing description and the examples which follow are intended to illustrate and not limit the scope of the invention. Other aspects, advantages and modifications within the scope of the invention will be apparent to those skilled in the art to which the invention pertains.

EXAMPLE 1

Polymer-bound polynucleoside H-phosphonates were prepared as described by Froehler et al., supra, on control pore glass using the DBU salt of the protected nucleoside H-phosphonate. The diester linkages were generated by aqueous $I_2$ oxidation and the amidate linkages by amine/$CCl_4$ oxidation. After two couplings the polynucleoside H-phosphonate was oxidized with a solution of 2-methoxyethylamine in Pyr/CCl₄ (1:5:5) (20 min.) followed by twelve more couplings and oxidation with aq. I₂ (0.1M in N-methyl morpholine/water/THF, 5:5:90) to generate a 15-mer containing two phosphoramidate linkages at the 3' end and twelve diester linkages. The oligomer was removed from the solid support, deprotected with conc. NH₄OH (45° C./18 hr.), and purified by HPLC (PRP) using an acetonitrile (CH₃CN) gradient in 50 mM aqueous TEAP. The DMT was removed from the product fraction (80% acetic acid/R.T./2 hrs.), evaporated, desalted and evaporated. Approximately 1 μg of purified product was 5' end-labeled with T4 polynucleotide kinase and γ-$^{32}$P ATP for further characterization.

EXAMPLE 2

Polymer-bound polynucleoside H-phosphonates were prepared as in the preceding example on control pore glass using the DBU salt of the protected nucleoside H-phosphonate. After twelve couplings the polynucleoside H-phosphonate was oxidized with aq. I₂ (0.1M in N-methyl morpholine/water/THF, 5:5:90) followed by two more couplings and oxidation with a solution of 2-methoxyethylamine in Pyr/CCl₄ (1:5:5) (20 min.) to generate a 15-mer containing twelve diester linkages at the 3' end and two phosphoramidate linkages at the 5' end. The oligomer was removed from the solid support, deprotected with conc. NH₄OH (45° C./18 hr.) and purified by HPLC (PRP) using an acetonitrile (CH₃CN) gradient in 50 mM aqueous TEAP. The DMT was removed from the product fraction (80% acetic acid/R.T./2 hrs.), evaporated, desalted and evaporated.

EXAMPLE 3

Polymer-bound polynucleoside H-phosphonates were prepared as described as in the preceding examples on control pore glass using the DBU salt of the protected nucleoside H-phosphonate. The diester linkages were generated by aqueous I₂ oxidation and the amidate linkages by amine/CCl₄. After two couplings the polynucleoside H-phosphonate was oxidized with a solution of 2-methoxyethylamine in Pyr/CCl₄ (1:5:5) (20 min.) followed by ten more couplings and oxidation with aq. I₂ (0.1M in N-methyl morpholine/water/THF, 5:5:90) to generate a 13-mer containing two phosphoramidate linkages at the 3' end and ten diester linkages. This was followed by two more couplings and oxidation with a solution of 2-methoxyethylamine in Pyr/CCl₄ (1:5:5) (20 min.) to generate a 15-mer containing two phosphoramidate linkages at the 3' end, ten diester linkages, and two phosphoramidate linkages at the 5' end. The oligomer was removed from the solid support and deprotected with conc. NH₄OH (45° C./18 hr.) and purified by HPLC (PRP) using an acetonitrile (CH₃CN) gradient in 50 mM aqueous TEAP. The DMT was removed from the product fraction (80% acetic acid/R.T./2 hrs.), evaporated, desalted and evaporated.

EXAMPLE 4

The procedure of Example 1 was repeated using dodecylamine to generate a 15-mer containing two phosphoramidate linkages at the 3' end and twelve diester linkages, wherein the phosphoramidate linkages are such that one of $R^1$ and $R^2$ as defined earlier herein is hydrogen and the other is dodecyl.

EXAMPLE 5

The procedure of Example 2 was repeated using dodecylamine in place of 2-methoxyethylamine, so as to yield a 15-mer containing twelve diester linkages at the 3' end and two phosphoramidate linkages at the 5' end, wherein the phosphoramidate linkages are substituted as in the preceding example, i.e., one of $R^1$ and $R^2$ is hydrogen and the other is dodecyl.

EXAMPLE 6

The procedure of Example 3 was repeated using dodecylamine in place of 2-methoxyethylamine, to give rise to a 15-mer containing two phosphoramidate linkages at the 3' end, ten diester linkages, and two phosphoramidate linkages at the 5' end, wherein the phosphoramidate is N-substituted as in the preceding two examples.

EXAMPLE 7

The procedure of Example 1 was repeated using propylamine to generate a 15-mer containing two phosphoramidate linkages at the 3' end and twelve diester linkages, wherein the phosphoramidate linkages are such that one of $R^1$ and $R^2$ as defined earlier herein is hydrogen and the other is n-propyl.

EXAMPLE 8

The procedure of Example 2 was repeated using propylamine in place of 2-methoxyethylamine, so as to yield a 15-mer containing twelve diester linkages at the 3' end and two phosphoramidate linkages at the 5' end, wherein the phosphoramidate linkages are substituted as in the preceding example, i.e., one of $R^1$ and $R^2$ is hydrogen and the other is n-propyl.

EXAMPLE 9

The procedure of Example 3 was repeated using propylamine in place of 2-methoxyethylamine, to give rise to a 15-mer containing two phosphoramidate linkages at the 3' end, ten diester linkages, and two phosphoramidate linkages at the 5' end, wherein the phosphoramidate is N-substituted as in the preceding two examples.

EXAMPLE 10

The following Example describes hybridization stability studies performed using end-capped oligonucleotides as described and claimed herein.

Oligonucleotides containing end-caps were tested for their ability to form stable duplexes with complementary single-stranded DNA sequences; the various oligonucleotides tested were outlined below in Table 1. Duplex stability was measured by determining the melting temperature $T_m$ in solution over a range of temperatures. The experiment was conducted in a solution containing 150 mM NaCl, 5 mM Na₂HPO₄ and 3 μM DNA at a pH of 7.1. The results obtained and set forth in Table 1 show that binding to complementary sequences is not materially affected by 3'-end-cap modification.

TABLE 1

| Compound | | $T_m$ (°C.) |
|---|---|---|

5' TCCAGTGATTTTTTTCTCCAT—O—P(=O)(—O—T—O—P(=O)(—O—T—OH)—HN—CH₂CH₂—OCH₃)—HN—CH₂CH₂—OCH₃  61.0
(MEA)

5' TCCAGTGATTTTTTTCTCCAT—O—P(=O)(—O—T—O—P(=O)(—O—T—OH)—HN—(CH₂)₁₁CH₃)—HN—(CH₂)₁₁CH₃  60.5
(C12)

5' TCCAGTGATTTTTTTCTCCAT—O—P(=O)(O⁻)—O—T—O—P(=O)(O⁻)—OH  61.5
(diester control)

EXAMPLE 11

Several additional oligonucleotides also end-capped at the 3' terminal two internucleotide linkages were tested for their ability to form stable duplexes with complementary single stranded DNA sequences, as described in the preceding example. Results are set forth in Table 2.

TABLE 2

| Compound | $T_m$ (°C.) |
|---|---|

5' TCTCCCTCTCTTT—O—P(=O)(NH—CH₂CH₂—OCH₃)—O—T—O—P(=O)(NH—CH₂CH₂—OCH₃)—O—T—OH  58.5
(methoxyethylamine)

5' TCTCCCTCTCTTT—O—P(=O)(O⁻)—O—T—O—P(=O)(O⁻)—O—T—OH  59.5

5' TCTCCCTCTCTTT—H  56.5
(diester)

EXAMPLE 12

The following example was used to determine the efficacy of end-capped oligodeoxynucleotides virus inhibition and cellular toxicity using oligonucleotides capped at two terminal 3'-end internucleotide linkages with 2-methoxyethylamine and dodecylamine.

The acute infection assay used the MOLT-4 cell line which is susceptible to HIV infection. Measurement of HIV p24 was used to assay for inhibition of virus replication 7 days after infection with virus at a multiplicity of infection of approximately 0.1. Approximately 1×10⁶ cells were preincubated with oligonucleotide, washed, infected with virus stock and then incubated for 7 days in oligonucleotide. HIV p24 levels in the supernatant were measured by radioimmunoassay and compared with control infections lacking oligonucleotide. Results are expressed as the percent of control p24 found in cultures containing oligonucleotide. Sequences of antisense oligonucleotides were complementary to HIV targets listed in Table 3. Toxicity data was obtained by incubation of 3'-end-capped oligonucleotides with uninfected cells, followed by a comparison with cell numbers with control cultures incubated in the absence of oligonucleotide. Toxicity results are expressed as the percent reduction of cell numbers obtained by incubation in oligonucleotide for 7 days compared to controls. The effective inhibition of HIV replication using low levels (0.5 to 5 μM) of capped oligodeoxynucleotides supports the conclusion that significant nuclease degradation of the oligonucleotides of the invention does not occur either extracellularly or intracellularly.

TABLE 3

| Target sequence | HIV Inhibition | Toxicity |
|---|---|---|
| PBS 5'AGAGATTTTCCACAC3' | | |
| -methoxyethylamine | | |
| 0.5 μM | 70% | 0% |
| 5.0 μM | 90% | 0% |
| 50.0 μM | — | 4% |
| -C12 | | |
| 0.5 μM | 0% | 0% |
| 5.0 μM | 90% | 2% |
| 50 μM | —* | 5% |
| NEF 5'TTGCCACCCATCTTA3' | | |
| -methoxyethylamine | | |
| 2.5 μM | 75% | 0% |
| 5.0 μM | 80% | 0% |
| 10.0 μM | 90% | 0% |
| 50 μM | | 0% |
| 100 μM | | 0% |
| propylamine | | |
| 2.5 μM | 65% | 0% |
| 5.0 μM | 80% | 0% |
| 50 μM | —* | 3% |
| 100 μM | —* | 3% |

*—not done under HIV inhibition column.

I claim:

1. An oligonucleotide resistant to degradation under physiological conditions, which oligonucleotide is a modified form of an oligonucleotide consisting essentially of nucleosides linked through phosphodiester linkages so that said phosphodiester linkages at the 3' terminus, or the 5' terminus, or both the 3' and 5' termini are replaced with N-substituted phosphoramidate linkages, the number of said replaced linkages being 1 to 10, wherein the phosphoramidate has the formula:

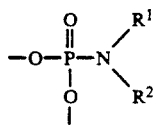

wherein $R^1$ and $R^2$ are independently selected from the group consisting of hydrogen, hydrocarbyl substituents of 20 carbon atoms or less, and oxyhydrocarbyl substituents of 20 carbon atoms or less containing 1 to 3 oxy groups, and wherein said hydrocarbyl or oxyhydrocarbyl substituents are linear or branched alkyl of 1 to 20 carbon atoms, linear or branched alkenyl of 2 to 20 carbon atoms, cycloalkyl or cycloalkenyl of 3 to 20 carbon atoms, linear or branched alkoxy of 1 to 20 carbon atoms, or aryl of 6 to 18 carbon atoms, provided that $R^1$ and $R^2$ are not both hydrogens.

2. The oligonucleotide of claim 1 wherein one of $R^1$ and $R^2$ is hydrogen and the other is an oxyhydrocarbyl substituent having the structure $CH_3-(CH_2)_x-$ wherein x is an integer in the range of 1 to 19, inclusive.

3. The oligonucleotide of claim 2 wherein x is 2 and the oxyhydrocarbyl substituent is 2-methoxyethyl.

4. The oligonucleotide of claim 1 wherein one of the $R^1$ and $R^2$ is hydrogen and the other is a straight-chain alkyl moiety having the formula $CH_3(Ch_2)_y-$ wherein y is an integer in the range of 0 to 15, inclusive.

5. The oligonucleotide of claim 4 wherein y is 11 and said alkyl substituent is dodecyl.

6. The oligonucleotide of claim 4 wherein y is 2 and said alkyl substituent is n-propyl.

7. The oligonucleotide of claim 1 wherein the number of said phosphoramidate linkages is less than that which lowers the melting temperature of the duplex formed with complement by less than about 10 degrees.

8. The oligonucleotide of claim 7 wherein the number of said phosphoramidate linkages is less than that which lowers the melting temperature of the duplex formed with complement by less than about 5 degrees.

9. The oligonucleotide of claim 2 wherein x is an integer in the range of 1 to 10, inclusive.

10. The oligonucleotide of claim 1, wherein the number of said replaced linkages is in the range of about 2 to 8.

11. The oligonucleotide of claim 10, wherein the number of said replaced linkages is in the range of about 2 to 6.

12. The oligonucleotide having the formula selected from the group consisting of:

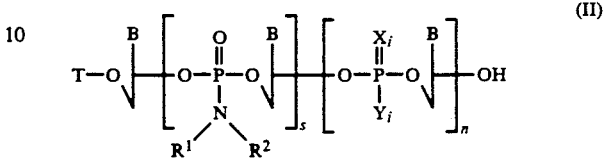

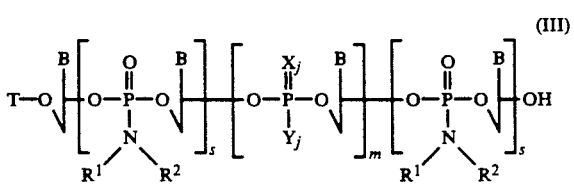

wherein each n, m, i, j and s is independently an integer and each s is in the range of about 2 to 10; each n and m is independently from 1 to about 50; s+n in formulas I and II is less than 100; and s+s+m in formula is less than 100; each i varies from 1 to n; each j varies from 1 to m; T is hydrogen or a hydroxyl-protecting group; $R^1$ and $R_2$ are independently selected from the group consisting of hydrogen, hydrocarbyl substituents of 20 carbon atoms or less, and oxyhydrocarbyl substituents of 20 carbon atoms or less containing 1 to 3 oxy groups, and wherein said hydrocarbyl or oxyhydrocarbyl substituents are linear or branched alkyl of 1 to 20 carbon atoms, linear or branched alkenyl of 2 to 20 carbon atoms, cycloalky or cycloalkenyl of 3 to 20 carbon atoms, linear or branched alkoxy of 1 to 20 carbon atoms, or aryl of 6 to 18 carbon atoms, with the proviso that $R^1$ to $R^2$ are not both hydrogen,
each B is independently a protected or unprotected heterocyclic base;
each $X_i$ and $X_j$ is independently O or S; and
each $Y_i$ and $Y_j$ is independently R, —SR or —OR, where R is as defined for $R^1$ and $R^2$.

13. The oligonucleotide of claim 12 wherein $X_i$ and $X_j$ are O and $Y_i$ and $Y_j$ are —OH.

14. The oligonucleotide of claim 12 wherein $X_i$ and $X_j$ are S and $Y_i$ and $Y_j$ are —OH.

15. The oligonucleotide of claim 12 wherein $X_i$ and $X_j$ are S and $Y_i$ and $Y_j$ are —SH.

16. The oligonucleotide of claim 12 wherein each n, m, i, j and s are integers in the range of about 2 to 10 and may be the same or different.

17. The oligonucleotide of claim 12 which is of formula (I) or (II).

18. The oligonucleotide of claim 17 wherein $X_i$ and $X_j$ are O and $Y_i$ and $Y_j$ are —OH.

19. The oligonucleotide of claim 17 wherein $X_i$ and $X_j$ are S and $Y_i$ and $Y_j$ are —OH.

20. The oligonucleotide of claim 17 wherein $X_i$ and $X_j$ are S and $Y_i$ and $Y_j$ are —SH.

* * * * *